United States Patent
Selter et al.

(10) Patent No.: US 11,731,346 B2
(45) Date of Patent: Aug. 22, 2023

(54) ADDITIVELY MANUFACTURING FLUORINE-CONTAINING POLYMERS

(71) Applicant: Honeywell Federal Manufacturing & Technologies, LLC, Kansas City, MO (US)

(72) Inventors: Thomas Matthew Selter, Blue Springs, MO (US); Jamie Michael Messman, Leawood, KS (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 0 days.

(21) Appl. No.: 17/490,210

(22) Filed: Sep. 30, 2021

(65) Prior Publication Data
US 2022/0016829 A1 Jan. 20, 2022

Related U.S. Application Data

(62) Division of application No. 16/806,494, filed on Mar. 2, 2020, now abandoned.

(51) Int. Cl.
*B29C 64/00* (2017.01)
*B29C 64/135* (2017.01)
(Continued)

(52) U.S. Cl.
CPC ............ *B29C 64/135* (2017.08); *B05D 5/083* (2013.01); *B22F 10/00* (2021.01); *B22F 10/85* (2021.01); *B22F 12/00* (2021.01); *B22F 12/82* (2021.01); *B29C 64/00* (2017.08); *B29C 64/10* (2017.08); *B29C 64/176* (2017.08); *B29C 64/182* (2017.08); *B29C 64/20* (2017.08); *B29C 64/205* (2017.08); *B29C 64/227* (2017.08); *B29C 64/245* (2017.08); *B29C 64/25* (2017.08); *B29C 64/255* (2017.08); *B29C 64/30* (2017.08); *B29C 64/307* (2017.08); *B29C 64/386* (2017.08); *B29C 64/393* (2017.08); *B29C 64/40* (2017.08);
(Continued)

(58) Field of Classification Search
CPC .............................. B29C 64/135; B33Y 10/00
See application file for complete search history.

(56) References Cited

U.S. PATENT DOCUMENTS

| | | | | |
|---|---|---|---|---|
| 2010/0113661 A1 * | 5/2010 | Senff | ...................... | C08G 69/44 524/261 |
| 2013/0171416 A1 * | 7/2013 | Diekmann | ............... | C08K 9/08 428/407 |

(Continued)

FOREIGN PATENT DOCUMENTS

| | | | | |
|---|---|---|---|---|
| CN | 106009430 | | 10/2016 | |
| JP | 3741966 B2 * | | 2/2006 | ....... G02F 1/133514 |

(Continued)

*Primary Examiner* — Nicholas R Krasnow
(74) *Attorney, Agent, or Firm* — Hovey Williams LLP

(57) ABSTRACT

A system and method of additively manufacturing a part including electrically conductive or static dissipating fluorine-containing polymers. The method includes depositing fluorine-containing polymer additive manufacturing material onto a build platform, selectively cross-linking portions of the deposited additive manufacturing material, and curing the selectively cross-linked portions such that the part is at least one of electrically conductive and static dissipating.

12 Claims, 4 Drawing Sheets

(51) Int. Cl.

| | |
|---|---|
| *B29C 64/20* | (2017.01) |
| *B33Y 10/00* | (2015.01) |
| *B33Y 70/00* | (2020.01) |
| *B33Y 30/00* | (2015.01) |
| *B33Y 80/00* | (2015.01) |
| *B22F 10/00* | (2021.01) |
| *B29C 64/307* | (2017.01) |
| *B29C 64/255* | (2017.01) |
| *B29C 64/245* | (2017.01) |
| *B33Y 99/00* | (2015.01) |
| *B29C 64/182* | (2017.01) |
| *B22F 12/00* | (2021.01) |
| *B29C 64/30* | (2017.01) |
| *B29C 64/386* | (2017.01) |
| *B33Y 40/10* | (2020.01) |
| *B33Y 40/00* | (2020.01) |
| *B29C 64/40* | (2017.01) |
| *B29C 64/25* | (2017.01) |
| *B29C 64/393* | (2017.01) |
| *B33Y 50/02* | (2015.01) |
| *B29C 64/205* | (2017.01) |
| *B33Y 40/20* | (2020.01) |
| *B33Y 50/00* | (2015.01) |
| *B22F 12/82* | (2021.01) |
| *B29C 64/10* | (2017.01) |
| *B29C 64/176* | (2017.01) |
| *B29C 64/227* | (2017.01) |
| *B22F 10/85* | (2021.01) |
| *B05D 5/08* | (2006.01) |
| *H01M 10/653* | (2014.01) |
| *C09D 5/24* | (2006.01) |
| *H01L 23/498* | (2006.01) |
| *H01M 4/66* | (2006.01) |
| *G03G 5/05* | (2006.01) |
| *G03G 5/07* | (2006.01) |
| *H05K 1/09* | (2006.01) |
| *H01B 1/00* | (2006.01) |
| *B29K 27/12* | (2006.01) |
| *B29K 507/04* | (2006.01) |
| *B01D 67/00* | (2006.01) |
| *G01N 33/00* | (2006.01) |
| *G03F 7/00* | (2006.01) |

(52) U.S. Cl.
CPC ............... *B33Y 10/00* (2014.12); *B33Y 30/00* (2014.12); *B33Y 40/00* (2014.12); *B33Y 40/10* (2020.01); *B33Y 40/20* (2020.01); *B33Y 50/00* (2014.12); *B33Y 50/02* (2014.12); *B33Y 70/00* (2014.12); *B33Y 80/00* (2014.12); *B33Y 99/00* (2014.12); *C09D 5/24* (2013.01); *G03G 5/05* (2013.01); *G03G 5/07* (2013.01); *H01B 1/00* (2013.01); *H01L 23/49883* (2013.01); *H01M 4/663* (2013.01); *H01M 10/653* (2015.04); *H05K 1/092* (2013.01); *B01D 67/00045* (2022.08); *B01D 67/00415* (2022.08); *B29K 2027/12* (2013.01); *B29K 2507/04* (2013.01); *G01N 2033/0095* (2013.01); *G03F 7/70416* (2013.01); *G03G 2215/2054* (2013.01); *G05B 2219/49023* (2013.01); *G05B 2219/49246* (2013.01); *H05K 2201/015* (2013.01); *H05K 2201/03* (2013.01); *Y10T 156/1722* (2015.01); *Y10T 156/1798* (2015.01)

(56) References Cited

U.S. PATENT DOCUMENTS

| | | | |
|---|---|---|---|
| 2015/0166694 A1 | 6/2015 | McCoy et al. | |
| 2016/0074938 A1* | 3/2016 | Kitani | B22F 12/37 219/76.12 |
| 2019/0030794 A1 | 1/2019 | Jiang et al. | |
| 2019/0030795 A1* | 1/2019 | Jiang | C09D 11/106 |

FOREIGN PATENT DOCUMENTS

| | | |
|---|---|---|
| WO | WO2004031458 | 4/2004 |
| WO | WO2015057783 | 4/2015 |

* cited by examiner

ADDITIVELY MANUFACTURING FLUORINE-CONTAINING POLYMERS

RELATED APPLICATIONS

The present patent application is a divisional patent application claiming priority benefit, with regard to all common subject matter, to U.S. patent application Ser. No. 16/806,494, entitled "ADDITIVELY MANUFACTURING FLUORINE-CONTAINING POLYMERS", filed Mar. 2, 2020. The earlier-filed patent application is hereby incorporated by reference in its entirety into the present application.

STATEMENT REGARDING FEDERALLY-SPONSORED RESEARCH OR DEVELOPMENT

This invention was made with Government support under Contract No.: DE-NA-0002839 awarded by the United States Department of Energy/National Nuclear Security Administration. The Government has certain rights in the invention.

BACKGROUND

Electrically conductive or static dissipating fluorine-containing polymer part manufacturing is currently limited by several factors. For example, internal stress in fluorine-containing polymers results in warping, particularly in larger fixtures. Conventional manufacturing with fluorine-containing polymers also produces volatile organic compounds (VOCs). Furthermore, general limitations of conventional manufacturing techniques such as material removal tooling restrictions prevent fluorine-containing polymers from being used in complex electronic circuits and other parts.

SUMMARY OF THE INVENTION

Embodiments of the present invention solve the above-mentioned problems and other problems and provide a distinct advance in the art of manufacturing electrically conductive or static dissipative parts. More particularly, the present invention provides a system and method for additively manufacturing parts including electrically conductive or static dissipating fluorine-containing polymers.

One embodiment of the invention is an additive manufacturing system comprising a build platform, a material deposition device, an energy source, and a cure device. The additive manufacturing system utilizes an additive manufacturing material including electrically conductive or static dissipating fluorine-containing polymers to form an electrically conductive or static dissipating part. The additive manufacturing system may employ any additive manufacturing or "3D printing" methods such as a sintering, laser melting, laser sintering, DIW, extrusion, fused filament, stereolithography, light polymerizing, powder bed, wire additive, or laminated object manufacturing. The additive manufacturing system may also be a hybrid system that combines additive manufacturing with molding, scaffolding, and/or other subtractive manufacturing or assembly techniques.

The additive manufacturing material may be in pellet or powder form or any other suitable form. The additive manufacturing material may also include a supplemental material such as graphite, graphene, or carbon.

The build platform may be a stationary or movable flat tray or bed, a substrate, a print plate, a shaped mandrel, a wheel, scaffolding, or similar support. The build platform may be integral with the additive manufacturing system or may be removable and transferable with the part as the part is being constructed.

The material deposition device may include a nozzle, guide, sprayer, or other similar component. The material deposition device may be configured to deposit material via direct ink writing (DIW) at room temperature for subsequent curing. In one embodiment, the material mixture deposition device is configured to extrude strands of additive manufacturing material mixture for creating a lattice structure.

The energy source may be a laser, heater, or similar component for melting the additive manufacturing material and bonding (e.g., sintering) the additive manufacturing material to a previously constructed layer. The energy source may be configured to melt the additive manufacturing material as the additive manufacturing material is being deposited or melt the additive manufacturing material of an entire layer after the layer of additive manufacturing material has been deposited.

The cure device is a heating device or system for curing the part after material deposition is complete. To that end, the cure device may be an oven, a furnace, a heating element, or any other suitable heating device.

In use, the build platform supports the part as it is being constructed. The material deposition device deposits the additive manufacturing material onto the build platform and onto previously constructed layers. The energy source bonds the additive manufacturing material together. The cure device cures the additive manufacturing material so as to create an electrically conductive or static dissipating part.

Another embodiment of the invention is a method of additive manufacturing a part using electrically conductive or static dissipating fluorine-containing polymers.

The additive manufacturing material is then fed to a material deposition device. The additive manufacturing material mixture may be metered in discrete amounts or continuously, depending on movement and position of the material deposition device.

A material deposition device then deposits the additive manufacturing material onto a build platform and previously constructed layers. The specific location and placement of the additive manufacturing material may be according to computer-aided design (CAD) data, or other technical model or drawing, as followed manually or by a user or as directed in an automated or semi-automated fashion via control signals provided from a processor. For example, the material deposition device may deposit the additive manufacturing material mixture according to an electronic circuit pattern.

The additive manufacturing material is then cured in a cure device or sintered via an energy source. For example, the cure device may heat the part so as to cross-link at least some of the deposited additive manufacturing material. This may be done selectively so that certain portions of the deposited additive manufacturing material are cross-linked. Alternatively, the energy source may melt or sinter, and thereby cross-link, selected portions of the additive manufacturing material of the current layer. This may include tracing the energy source over or through the current layer according to CAD data, models, drawings, or other technical resources. A drying system may then be used to dry (or post cure) the part.

Any of the above steps may be repeated multiple times as needed. For example, once one layer of the part has been deposited, another layer of additive manufacturing material may be deposited on the previously deposited layer.

The above-described steps may be performed in any order, including simultaneously. In addition, some of the steps may be repeated, duplicated, and/or omitted without departing from the scope of the present invention.

The above-described additive manufacturing system and method provide several advantages. For example, the resulting part is at least one of electrically conductive and static dissipating, while benefiting from the broad possibilities of additive manufacturing and design. A functional material may be selectively added to the additive manufacturing material, thus training the electrically conductive or static dissipating characteristic in regions, portions, or areas of the part for creating electronic circuits and other electrical or static-sensitive components. For other applications, the electrically conductive or static dissipating characteristic can be truly homogenous throughout the additive manufacturing material (and hence the part), whereas conventional manufacturing techniques only provide approximate homogeneity.

Additive manufacturing reduces internal stresses in the electrically conductive or static dissipating fluorine-containing polymers and allows this material to be used in larger fixtures without warping. It also reduces the release of volatile organic compounds. Additive manufacturing with electrically conductive or static dissipating fluorine-containing polymers can be used at least in several electronic circuit and electronic assembly applications, cleaning (e.g., cleaning fixtures that are ESD compliant), and electrical encapsulation.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
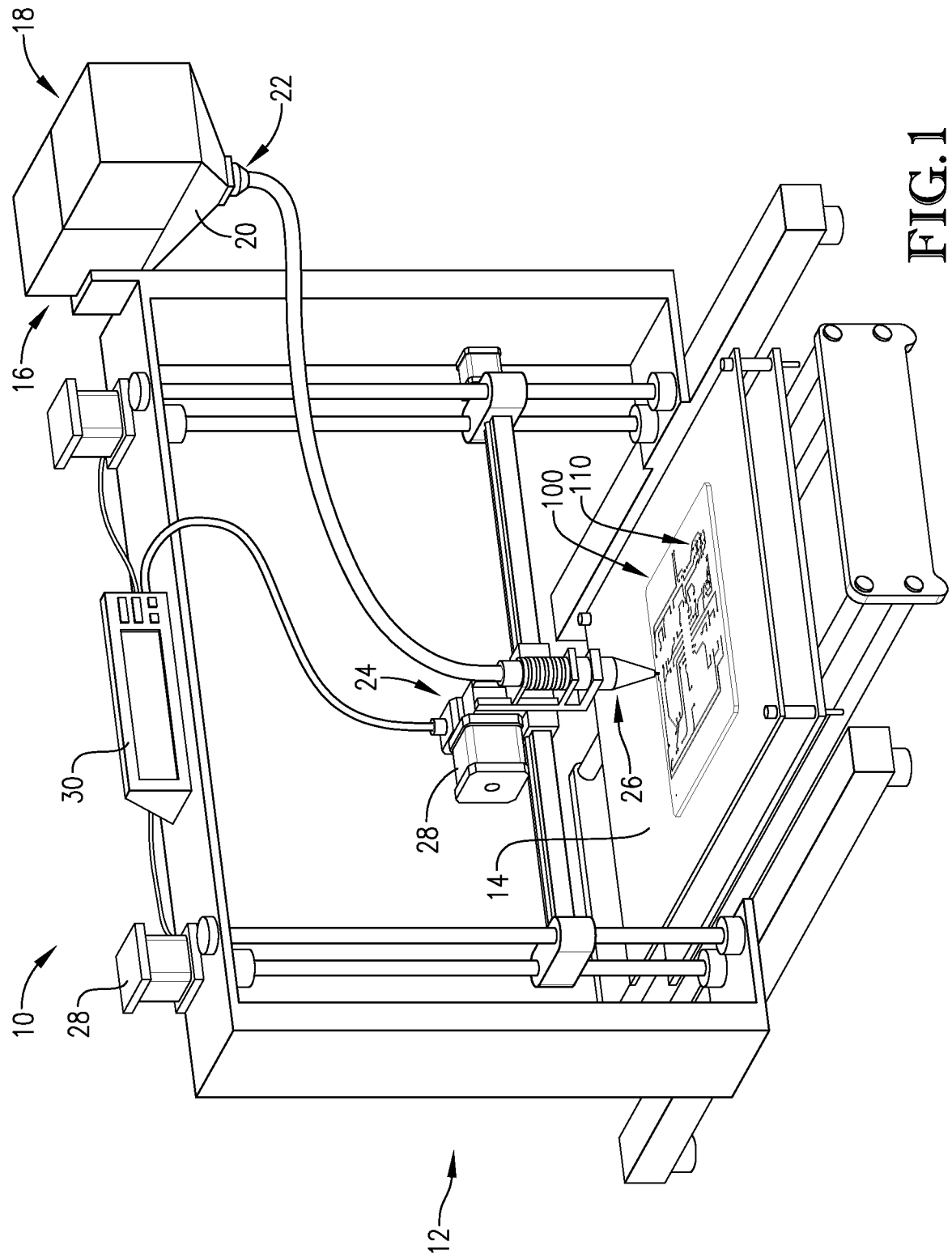
FIG. 1 is a perspective view of an additive manufacturing system constructed in accordance with an embodiment of the invention.
Figure 2:
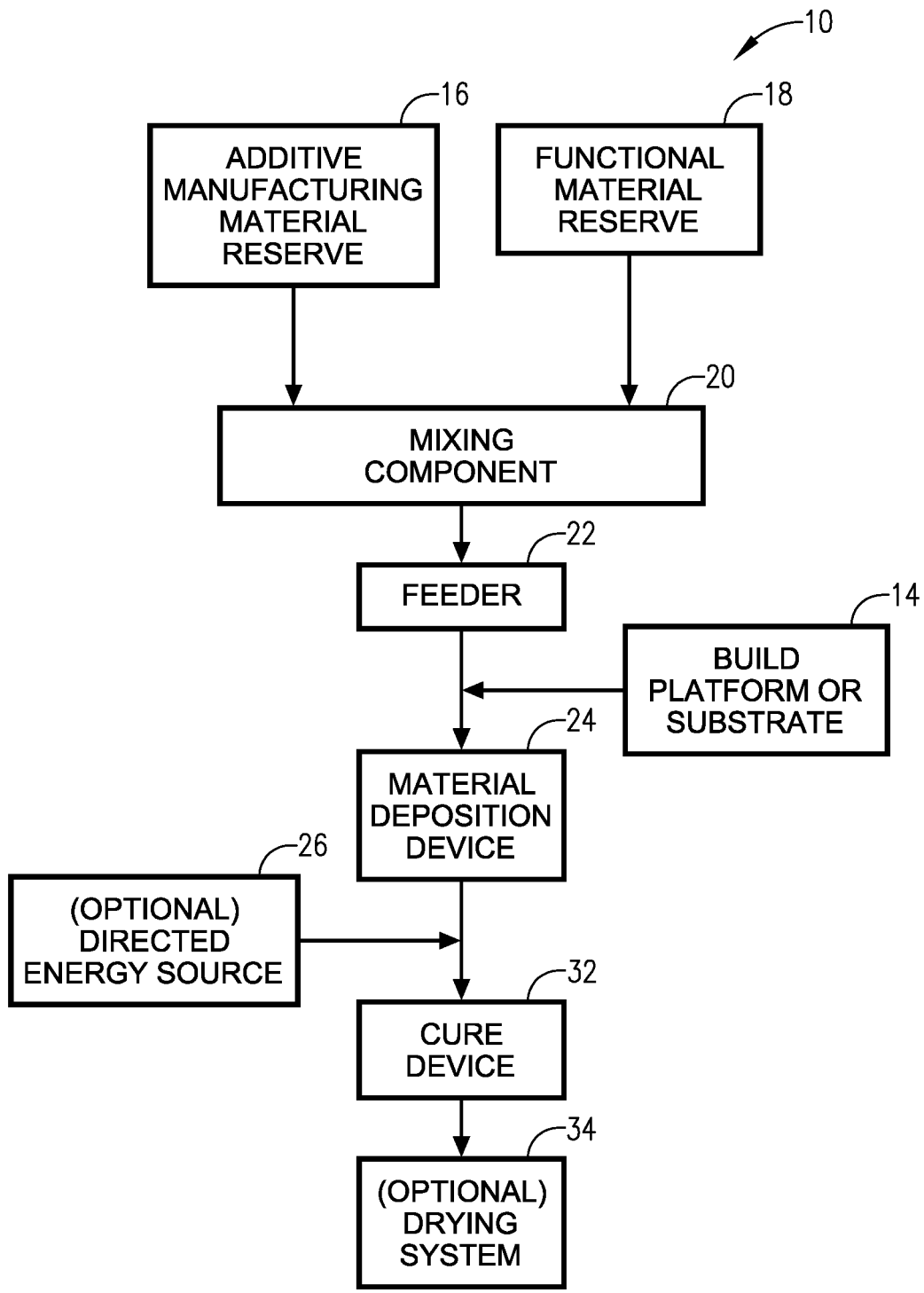
FIG. 2 is a schematic diagram of components of the additive manufacturing system of FIG. 1.
Figure 3:
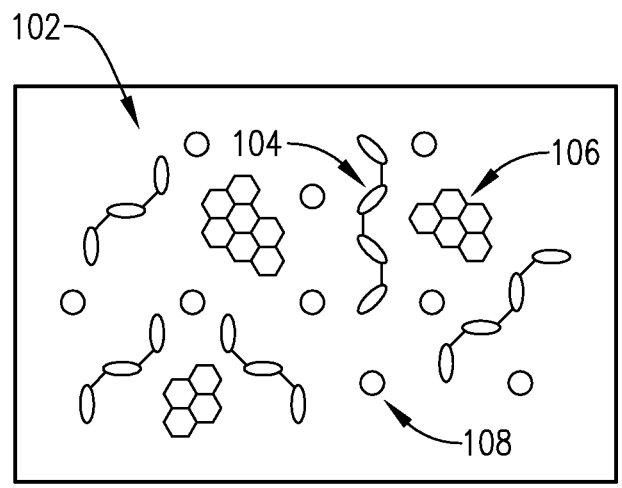
FIG. 3 is an enlarged view of an additive manufacturing material mixture including an additive manufacturing material having fluorine-containing polymers mixed with a supplemental material, and a mix-promoting functional material, in accordance with an embodiment of the invention.
Figure 4:
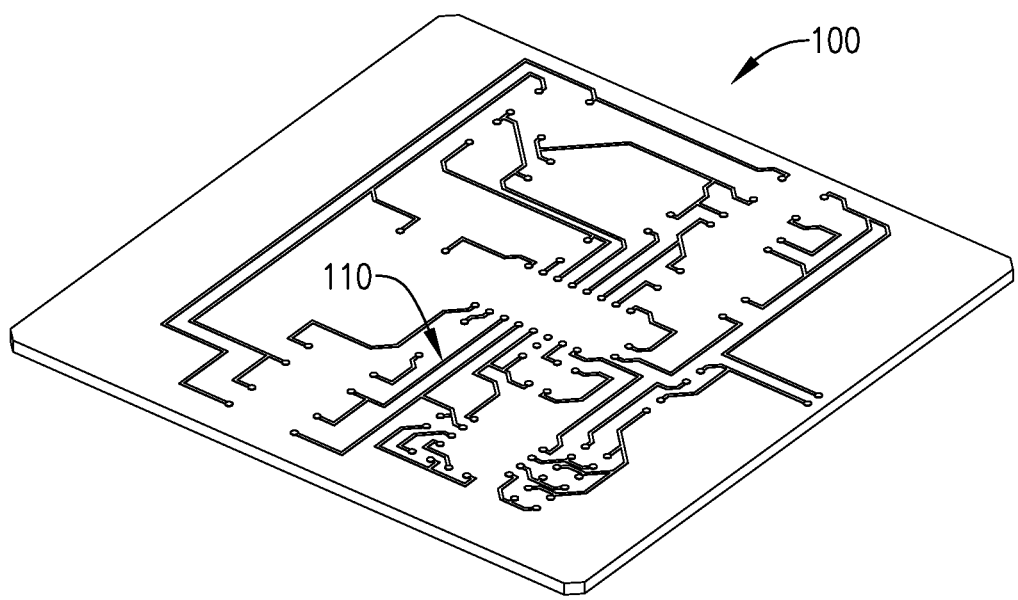
FIG. 4 is a perspective view of a part formed via the additive manufacturing material mixture of FIG. 3 in accordance with an embodiment of the invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Turning to the drawing figures, and particularly FIGS. 1-4, an additive manufacturing system 10 constructed in accordance with an embodiment of the present invention is illustrated. The additive manufacturing system 10 may employ any additive manufacturing or "3D printing" methods such as a sintering, laser melting, laser sintering, DIW, extrusion, fused filament, stereolithography, light polymerizing, powder bed, wire additive, or laminated object manufacturing. The additive manufacturing system 10 may also be a hybrid system that combines additive manufacturing with molding, scaffolding, and/or other subtractive manufacturing or assembly techniques. The additive manufacturing system 10 broadly comprises a frame 12, a build platform 14, an additive manufacturing material reserve 16, a functional material reserve 18, a mixing component 20, a feeder 22, a material deposition device 24, an optional energy source 26, a set of motors 28, a processor 30, a cure device 32, and an optional drying system 34.

The frame 12 provides structure for at least the build platform 14, feeder 22, material mixture deposition device 24, energy source 26, and motors 28 and may include a base, vertical members, cross members, and mounting points for mounting the above components thereto. Alternatively, the frame 12 may be a walled housing or similar structure.

The build platform 14 supports a part 100 as it is constructed and may be a stationary or movable flat tray or bed, a substrate, a print plate, a shaped mandrel, a wheel, scaffolding, or similar support. The build platform 14 may be integral with the additive manufacturing system 10 or may be removable and transferable with the part 100 as the part 100 is being constructed.

The additive manufacturing material reserve 16 retains additive manufacturing material 102 and may be a hopper, tank, cartridge, container, spool, or other similar material holder. The additive manufacturing material reserve 16 may be integral with the additive manufacturing system 10 or may be disposable and/or reusable.

The additive manufacturing material 102 includes fluorine-containing polymers 104 and a supplemental material 106. The fluorine-containing polymers 104 may be polytetrafluoroethylene (PTFE), fluorinated ethylene propylene (FEP), perfluoroalkoxy (PFA), ethylene tetrafluoroethylene (ETFE), or any other suitable fluorine-containing polymer.

We should consider the supplemental material be graphite, graphene, carbon, or any other suitable supplemental material and any combination of the supplemental materials. The supplemental material 106 may be graphite, graphene, carbon, or any other suitable supplemental material. The supplemental material 106 may be added to, stirred in, or blended with the additive manufacturing material 102 as a doping agent or the like. The supplemental material 106 may be between 1% and 65%, between 5% and 55%, or between 15% and 50% by weight. In one embodiment, the supplemental material 106 is graphene between 20% and 25% by weight. In another embodiment, the supplemental material 106 is carbon between 40% and 55% by weight. In yet another embodiment, the supplemental material 106 is graphite between 35% and 45% by weight. In one embodiment, the supplemental material 106 is a virgin material. In yet another embodiment, the supplemental material 106 is saturated in the additive manufacturing material 102.

The functional material reserve 18 retains the functional material 108 and may be a hopper, tank, cartridge, container, spool, or other similar material holder. The functional material reserve 18 may be integral with the additive manufacturing system 10 or may be disposable and/or reusable.

The functional material 108 may be any suitable fluorinating agent for promoting mixing of the fluorine-containing polymers 104 and the supplemental material 106 of the additive manufacturing material. The functional material 108 may be mixed with the additive manufacturing material 102 via the mixing component 20 or may be pre-mixed with the additive manufacturing material 102.

The mixing component 20 is connected downstream of the additive manufacturing material reserve 16 and the functional material reserve 18 and upstream of the feeder 22. The mixing component 20 combines, via continuous inline mixing, batch mixing, or the like, the functional material 108 with the fluorine-containing polymers 104 and the supplemental material 106 of the additive manufacturing material 102 to form a homogenous mixture. The mixing component 20 may be a mechanical mixer, a planetary mixer, a resonance acoustic mixer, or any other suitable mixer.

The feeder 22 is connected downstream of the mixing component 20 and directs the additive manufacturing material 102 (now as a mixture) to the material deposition device 24. The feeder 22 may be a pump, an auger, or any other suitable feeder. Alternatively, the additive manufacturing material 102 may be gravity fed to the material deposition device 24.

The material deposition device 24 may include a nozzle, guide, sprayer, rake, or other similar component for depositing the additive manufacturing material mixture onto the build platform 14 and previously constructed layers via DIW or a similar technique. In one embodiment, the material deposition device 24 prints strands of additive manufacturing material 102 to create a lattice structure.

The optional energy source 26 may be a laser, heater, or similar component for melting the additive manufacturing material 102 and bonding (e.g., sintering) the additive manufacturing material 102 to a previously constructed layer. The energy source 26 may be configured to melt the additive manufacturing material 102 as the additive manufacturing material 102 is being deposited or melt the additive manufacturing material 102 of an entire layer after the layer of additive manufacturing material 102 has been deposited. The energy source 26 may be a directed energy source configured to selectively melt portions of the additive manufacturing material 102.

The motors 28 position the material deposition device 24 over the build platform 14 and previously constructed layers and move the material deposition device 24 as the additive manufacturing material 102 is deposited onto the build platform 14 and the previously constructed layers. The motors 28 may be oriented orthogonally to each other so that a first one of the motors 28 is configured to move the material deposition device 24 in a lateral "x" direction, a second one of the motors 28 is configured to move the material deposition device 24 in a longitudinal "y" direction, and a third one of the motors 28 is configured to move the material deposition device 24 in an altitudinal "z" direction. Alternatively, the motors 28 may move the build platform 14 (and hence the part 100) while the material deposition device 24 remains stationary.

The processor 30 directs the material deposition device 24 via the motors 28 and activates the material deposition device 24 such that the material deposition device 24 deposits the additive manufacturing material 102 onto the build platform 14 and previously constructed layers according to a computer aided design of the part. The processor 30 may include a circuit board, memory, display, inputs, and/or other electronic components such as a transceiver or external connection for communicating with other external computers.

The processor 30 may implement aspects of the present invention with one or more computer programs stored in or on computer-readable medium residing on or accessible by the processor. Each computer program preferably comprises an ordered listing of executable instructions for implementing logical functions in the processor 30. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The cure device 32 may be a heating device or system for curing the part 100 after deposition is complete. The cure device 32 may be an oven, a furnace, a heating element, or any other suitable heating device. The cure device 32 heats the part 100 so as to crosslink polymers in the additive manufacturing material 102.

The optional drying system 34 may use heat, positive airflow, humidity control, or a combination thereof to dry the part 100. Alternatively, the part 100 may be air-dried.

Figure 5:
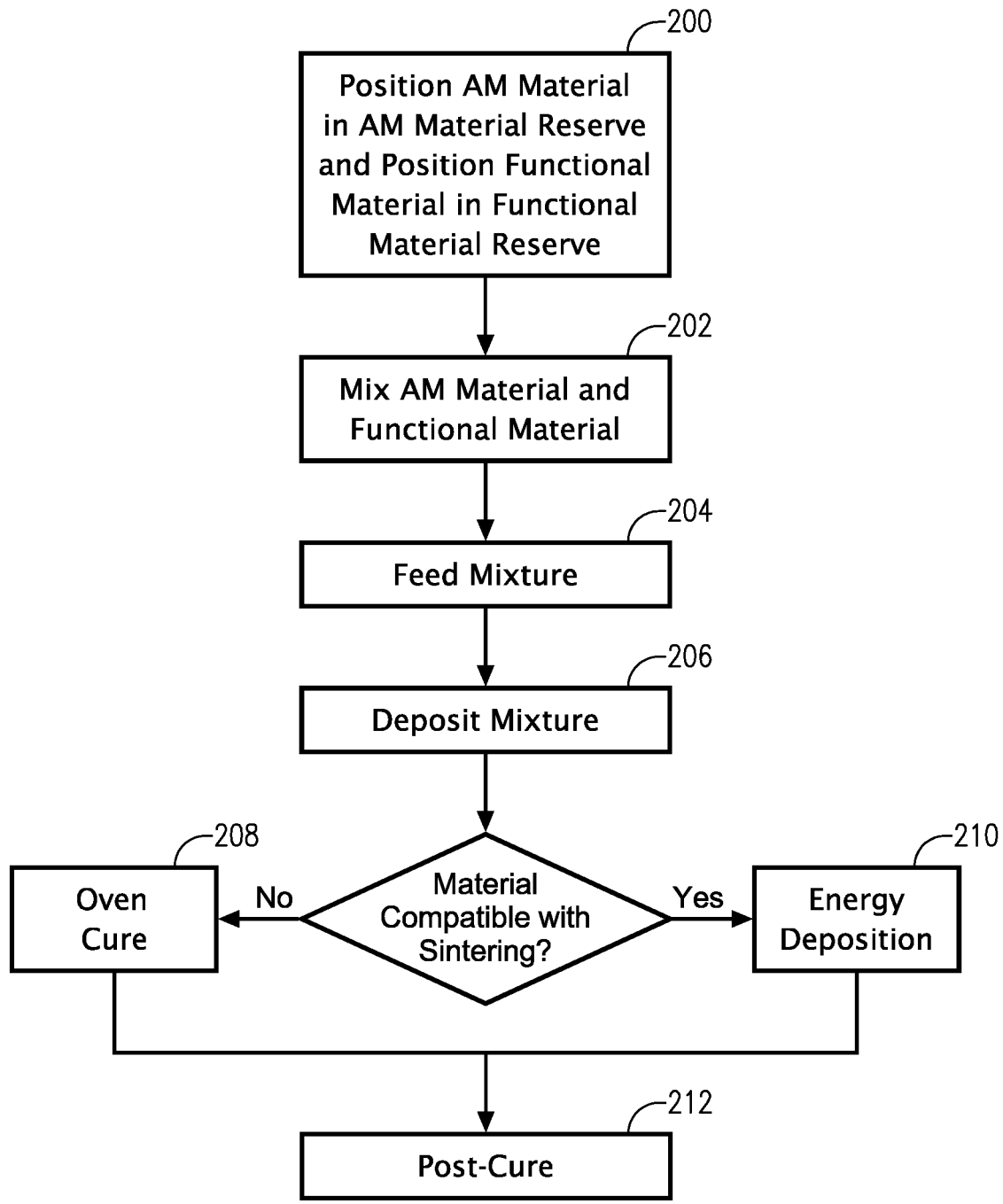
FIG. 5 is a flow diagram showing some steps of a method of forming a part via additive manufacturing in accordance with another embodiment of the invention.

Turning to FIG. 5, and with reference to FIGS. 1-4, use of the additive manufacturing system 10 will now be described in more detail. First, the additive manufacturing material 102 may be positioned in the additive manufacturing material reserve 16 and the functional material 108 may be positioned in the functional material reserve 18, as shown in block 200.

The additive manufacturing material 102 (including the fluorine-containing polymers 104 and the supplemental material 106) and the functional material 108 may then be mixed together via the mixing component 20 to create a homogenous additive manufacturing material mixture, as shown in block 202. The functional material 108 promotes mixing of the fluorine-containing polymers 104 and the supplemental material 106. The mixing component 20 may selectively add the functional material 102 to the additive manufacturing material 102 according to computer-aided design (CAD) data, or other technical model or drawing, as followed manually or by a user or as directed in an automated or semi-automated fashion via control signals provided from the processor 30 to the motors 28. For example, the mixing component may add the functional material 102 to the additive manufacturing material 102 according to an electronic circuit pattern.

The additive manufacturing material mixture may then be fed to the material deposition device 24 via the feeder 22, as shown in block 204. The additive manufacturing material mixture may be metered in discrete amounts or continuously, depending on movement and position of the material deposition device 24.

The material deposition device 24 may then deposit the additive manufacturing material mixture onto the build platform 14 and previously constructed layers, as shown in block 206. The specific location and placement of the additive manufacturing material mixture may be according to computer-aided design (CAD) data, or other technical model or drawing, as followed manually or by a user or as directed in an automated or semi-automated fashion via control signals provided from the processor 30 to the motors 28. For example, the material deposition device 24 may then deposit the additive manufacturing material mixture according to an electronic circuit pattern. In one embodiment, the additive manufacturing material mixture is extruded as strands so that the resulting part includes a lattice structure.

In one embodiment, if the additive manufacturing material 102 is incompatible with sintering, the additive manufacturing material 102 may be cured in the cure device 32, as shown in block 208. To that end, the cure device 32 may heat the part 100 so as to cross-link at least some of the deposited additive manufacturing material 102. This may be done selectively so that certain portions of the deposited additive manufacturing material 102 are cross-linked. Alternatively, the additive manufacturing material 102 may be allowed to passively cure (e.g., at room temperature). However, doing so may consume more time. In another embodiment, the additive manufacturing material 102 may be heat cured during processing.

In another embodiment, if the additive manufacturing material 102 is compatible with sintering, the optional energy source 26 may melt or sinter, and thereby cross-link, selected portions of the additive manufacturing material 102 of the current layer, as shown in block 210. This may include tracing the energy source 26 over or through the current layer according to CAD data, models, drawings, or other technical resources. The additive manufacturing material 102 may fuse together and to additive manufacturing material of a previous layer. Temperature ranges for this step are selected to prevent deterioration of the additive manufacturing material 102.

Note that any of steps 200-210 may be repeated multiple times as needed. For example, once one layer of the part has been deposited, another layer of additive manufacturing material may be deposited on the previously-deposited layer. This may be accomplished through first lowering the build platform 14 relative to the material deposition device 24 and energy source 26.

The optional drying system 34 may then dry (or post cure) the part, as shown in block 212. To that end, the part may be dried via heat, positive airflow, humidity control, or a combination thereof. Alternatively, the part may be air-dried.

The above-described steps may be performed in any order, including simultaneously. In addition, some of the steps may be repeated, duplicated, and/or omitted without departing from the scope of the present invention.

The above-described additive manufacturing system 10 and method provide several advantages. For example, the resulting part is at least one of electrically conductive and static dissipating, while benefiting from the broad possibilities of additive manufacturing and design. The functional material 108 promotes mixing of the fluorine-containing polymers 104 with the supplemental material 106 in a fluorination process. When the functional material 108 is added selectively, the electrically conductive or static dissipating characteristic can thereby be trained in regions, portions, or areas of the part for creating electronic circuits (such as electronic circuit 110) and other electrical or static-sensitive components. For other applications, the electrically conductive or static dissipating characteristic can be truly homogenous throughout the additive manufacturing material 102 (and hence the part), whereas conventional manufacturing techniques only provide approximate homogeneity.

Additively manufacturing reduces internal stresses in the electrically conductive or static dissipating fluorine-containing polymers and allows this material to be used in larger fixtures without warping. It also reduces the release of volatile organic compounds. Additive manufacturing with electrically conductive or static dissipating fluorine-containing polymers can be used at least in several electronic circuit and electronic assembly applications, cleaning (e.g., cleaning fixtures that are ESD compliant), and electrical encapsulation.

Although the invention has been described with reference to the embodiments illustrated in the attached drawing figures, it is noted that equivalents may be employed and substitutions made herein without departing from the scope of the invention as recited in the claims.

The invention claimed is:

1. A method of forming a part via additive manufacturing, the method comprising steps of:
   selectively adding a functional material to an additive manufacturing material according to an electronic circuit pattern to form an additive manufacturing material mixture to enhance mixing of a supplemental material of the additive manufacturing material with fluorine-containing polymers of the additive manufacturing material, the fluorine-containing polymers having at least one of an electrically conductive characteristic and a static dissipating characteristic;
   depositing the additive manufacturing material and the additive manufacturing material mixture onto a build platform such that the at least one of the electrically conductive characteristic and the static dissipating characteristic of the fluorine-containing polymers is trained in at least one of regions, portions, and areas of the part via the selective adding of the functional material according to the electronic circuit pattern; and curing the deposited additive manufacturing material.

2. The method of claim 1, the supplemental material being at least one of graphite, graphene, and carbon.

3. The method of claim 2, wherein the at least one of graphite, graphene, and carbon is saturated in the additive manufacturing material.

4. The method of claim 1, wherein the part is an electronic assembly.

5. The method of claim 1, wherein the part is an electrical encapsulation.

6. A method of forming a part via additive manufacturing, the method comprising steps of:

delivering from an additive manufacturing material reserve an additive manufacturing material including fluorine-containing polymers and a supplemental material, the fluorine-containing polymers having at least one of an electrically conductive characteristic and a static dissipating characteristic, the supplemental material including at least one of graphite, graphene, and carbon;

delivering from a functional material reserve a functional material configured to enhance mixing of the fluorine-containing polymers with the supplemental material when the functional material is added to the additive manufacturing material;

selectively adding, via a mixer downstream of the additive manufacturing material reserve and the functional material reserve, the functional material to the additive manufacturing material according to an electronic circuit pattern to form an additive manufacturing material mixture to enhance mixing of the supplemental material with the fluorine-containing polymers;

depositing the additive manufacturing material and the additive manufacturing material mixture onto a build platform such that the at least one of the electrically conductive characteristic and the static dissipating characteristic is trained in at least one of regions, portions, and areas of the part via the selective adding of the functional material according to the electronic circuit pattern; and curing the deposited additive manufacturing material.

7. The method of claim 6, wherein the selectively cross-linking step is performed via stereolithography.

8. The method of claim 6, wherein the additive manufacturing material and functional material are powders.

9. The method of claim 6, wherein the at least one of graphite, graphene, and carbon is saturated in the additive manufacturing material.

10. The method of claim 6, wherein the part is an electronic assembly.

11. The method of claim 6, wherein the part is an electrical encapsulation.

12. A method of forming a part via additive manufacturing, the method comprising steps of:

delivering from an additive manufacturing material reserve a powdered additive manufacturing material including fluorine-containing polymers and a supplemental material, the fluorine-containing polymers having at least one of an electrically conductive characteristic and a static dissipating characteristic, the supplemental material including at least one of graphite, graphene, and carbon saturated in the additive manufacturing material;

delivering from a functional material reserve a powdered functional material configured to promote mixing of the fluorine-containing polymers with the supplemental material when added to the additive manufacturing material;

selectively adding, via a mixer downstream of the additive manufacturing material reserve and the functional material reserve, the functional material to the additive manufacturing material according to an electronic circuit pattern to form an additive manufacturing material mixture to enhance mixing of the supplemental material with the fluorine-containing polymers;

depositing the additive manufacturing material and the additive manufacturing material mixture onto a build platform via a deposition device downstream of the mixer such that the at least one of the electrically conductive characteristic and the static dissipating characteristic is trained in at least one of regions, portions, and areas of the part via the selective adding of the functional material according to the electronic circuit pattern; and curing the deposited additive manufacturing material.

* * * * *